United States Patent [19]

Abramson et al.

[11] Patent Number: 4,465,636

[45] Date of Patent: Aug. 14, 1984

[54] PROCESS FOR THE MANUFACTURE OF ALKYL VANADATES

[75] Inventors: Alan J. Abramson; Gershon J. Davis, both of White Plains, N.Y.

[73] Assignee: Stauffer Chemical Company, Westport, Conn.

[21] Appl. No.: 416,817

[22] Filed: Sep. 13, 1982

[51] Int. Cl.$^3$ .................................. C07F 9/00
[52] U.S. Cl. ..................................... 260/429 R
[58] Field of Search ............................ 260/429 R

[56] References Cited

U.S. PATENT DOCUMENTS

| 1,133,961 | 3/1915 | Hess | 260/429 R |
|---|---|---|---|
| 2,220,041 | 10/1940 | Hill | 260/429 R |
| 2,257,009 | 9/1941 | Hill | 260/429 R |
| 3,652,617 | 3/1972 | Termin et al. | 260/429 R |
| 3,657,295 | 4/1972 | McCoy | 260/429 R |
| 3,920,751 | 11/1975 | Chabardes et al. | 260/429 R X |
| 3,987,074 | 10/1976 | Haase et al. | 260/429 R |
| 4,014,911 | 3/1977 | Muntz et al. | 260/429 R |
| 4,014,912 | 3/1977 | Muntz et al. | 260/429 R |
| 4,351,775 | 9/1982 | Magee | 260/429 R |

*Primary Examiner*—Helen M. S. Sneed
*Attorney, Agent, or Firm*—Richard P. Fennelly

[57] ABSTRACT

The yield of alkyl vanadate formed by the reaction of vanadium pentoxide and an alkyl alcohol in the presence of an azeotroping agent and, preferably, a catalyst is improved by the present invention. It involves lowering, prior to the reaction, the amount of vanadium having a valence lower than +5 in the vanadium pentoxide reagent.

14 Claims, No Drawings

PROCESS FOR THE MANUFACTURE OF ALKYL VANADATES

BACKGROUND OF THE INVENTION

1. Field of the Invention

The present invention is a process for improving the yields in a process for forming alkyl vanadates by the reaction of vanadium pentoxide and an alkyl alcohol in the presence of an azeotroping solvent.

2. Description of the Prior Art

Alkyl vanadates, which are useful as catalysts, can be formed by the reaction of vanadium pentoxide and an alkyl alcohol with by-product water being removed by an azeotroping solvent to help drive the reaction to completion. For example, benzene has been suggested for use as an azeotroping solvent in Bull. Acad. Sci. U.S.S.R. 1959, pp. 899-900 and in U.S. Pat. No. 3,920,751 to P. Charbardes et al. (Examples 5-6). Also suggested as a suitable azeotroping solvent is toluene (U.S. Pat. No. 3,657,295 to D. R. McCoy). More recently, alkane azeotroping solvents have been suggested (W. Magee, U.S. Ser. No. 245,868, filed Mar. 20, 1981).

Other methods for removing by-product water have been suggested to the exclusion of using an azeotroping solvent. In U.S. Pat. No. 3,987,074 to R. Haase et al., for example, the reaction of vanadium pentoxide and alkyl alcohol is conducted in the presence of an orthoester of the formula $RC(OR')_3$, where R is hydrogen or $C_1$-$C_5$, and R' are each independently $C_1$-$C_{12}$ or phenyl. In the Haase patent it is mentioned that prior art attempts to use strongly acidic catalysts promote the reduction of pentavalent vanadium to tetravalent vanadium and that such a side reaction is not desired. The Haase et al. process is described as one in which any unreacted vanadium pentoxide contains tetravalent vanadium on "only a negligible scale" so that it is not necessary to regenerate the pentoxide after each batch.

SUMMARY OF THE PRESENT INVENTION

The present invention resides in the discovery that yield improvement can be achieved in the reaction of vanadium pentoxide and alkyl alcohol, using an azeotroping solvent, if the amount of vanadium having a valence of below +5 is lowered in the vanadium pentoxide prior to the reaction to achieve such increase in yield. Preferably the reaction is conducted using an alkane solvent, e.g., heptane, and a basic nitrogenous catalyst. The process does not involve use of the type of orthoester described by Haase et al. to remove by-product water.

DESCRIPTION OF THE PREFERRED EMBODIMENTS

The reactants that are used in practicing the present invention, i.e. vanadium pentoxide and an alkyl alcohol, will depend upon the alkyl group desired in the alkyl vanadate product. Use of alkyl alcohols containing any of the $C_2$ to $C_6$ straight or branched alkyl groups is contemplated in accordance with the present invention. Branched chain alcohols are generally preferred, since they yield a vanadate product having improved thermal stability. Representative examples of such alkyl alcohols include ethanol, butanol, isobutanol, amyl alcohol, and isoamyl alcohol. The use of an excess amount of alcohol is preferred since it tends to increase the rate of reaction. Generally, the mole ratio of alkyl alcohol to vanadium pentoxide can vary from about 3:1 to 12:1.

In accordance with the present invention a suitable azeotroping agent is used to assist in the removal of by-product water from the reaction medium and thus help drive the reaction to completion. Examples of suitable aromatic solvents that have been proposed by various prior art investigators include toluene and benzene. It is, however, preferred to use a $C_6$-$C_8$ alkane azeotroping solvent, such as heptane, as described in U.S. Pat. No. 4,351,775, which is incorporated herein by reference. Examples of other suitable alkane solvents (which boil at about 60°-130° C.) are hexane, octane, isooctane and cyclohexane.

In selecting the particular azeotroping agent, one should select one which insures that by-product water from the reaction will preferentially co-distill with the solvent at a high concentration of water. The boiling point of the alcohol should also be high enough to ensure that it is present to assist in the removal of the water when the reaction is taking place. Its boiling point should not be so high as to decompose the desired vanadate product or to require the input of excessive amounts of heat energy to initiate and sustain the desired reaction. It is also preferred, in certain embodiments, that the solvent be less dense that water to produce water as the bottom or heavier phase in the separation apparatus to assist in its removal. Generally, the amount of azeotroping solvent to alcohol, for example, can range from about 0.05:1 to about 3:1 on a weight basis.

Also preferred in the process of the present invention is the use of a catalytically effective amount of a basic nitrogenous compound. The basic nitrogenous compound is one which is capable of providing a basic nucleophilic entity to the reaction medium to catalyze the reaction. Compounds having a structure in which the electron pair on the nitrogen atom is readily available are preferred. Basic nitrogenous compounds having double bonds between the nitrogen atom or atoms and an adjacent carbon atom, or which have a carbonyl group on the adjacent carbon atom, are not preferred since they are less effective as catalysts. Also, the use of relatively insoluble basic nitrogenous compounds is not preferred for the same reason. In general terms, the amount of such catalyst can range from about 0.1% to about 25%, by weight, or more, of the vanadium pentoxide content. The upper limit is principally dictated by economic considerations and also by the possibility that at such higher concentrations, the compounds may release excessive amounts of ammonia from the reaction.

Examples of some suitable basic nitrogenous compounds include ammonia; ammonium compounds, such as ammonium hydroxide, ammonium carbonate, ammonium phosphate (dibasic), and ammonium metavanadate; amine compounds, such as triethylamine; the dialkyl formamide compounds, such as dimethyl formamide; urea; pyridine; guanidine carbonate; and the like.

In accordance with the improvement of the present invention, the yield of alkyl vanadate formed in the above type of reaction is improved significantly by insuring a very low amount of vanadium of reduced species in the vanadium pentoxide. As demonstrated in the Examples, the yield of alkyl vanadate can increase dramatically from about the neighborhood of 50% or so with a 0.7-0.8% level of reduced vanadium in the vanadium pentoxide to a yield of 90% to 98% for a level in the neighborhood of just under 0.1%. The presence of unacceptably high levels of reduced vanadium can generally be determined visually by the presence of a dark brownish tint to the otherwise more orange color of the purer pentoxide reagent.

The reduced vanadium species in the pentoxide can be lowered by any means known to persons of ordinary skill in the art. For example, if the vanadate producer is not the manufacturer of the vanadium pentoxide reagent, such producer can require the manufacturer to assure a negligible content of $V^{+4}$ and lower species in the pentoxide reagent. If the vanadate producer also controls manufacture of the pentoxide, such producer can also insure the highest level of $V^{+5}$ species by such means, for example, as insuring the most complete oxidation of vanadium or ammonium metavanadate when either is converted to the pentoxide form. This can be done, for example, by reducing the throughput for the oxidation process. It is also possible to regenerate vanadium pentoxide having a higher than desired content of valence species lower than $V^{+5}$ by treatment with a suitable oxidizing agent such as air or oxygen. It is preferred to have the amount of vanadium having a valence lower than +5 held to no more than about 0.2%, by weight of the vanadium pentoxide.

After the vanadium pentoxide reagent has had its amount of reduced species vanadium lowered to the type of low amounts described herein, the process for forming the vanadate can be begun. It is preferred that the reaction be conducted by admixing the desired quantities of vanadium pentoxide, alkyl alcohol, solvent, and catalyst in a reaction vessel and refluxing the contents of the reactor while preferably maintaining an inert gas blanket over the reaction mixture during the initial stages of the reaction. During the refluxing operation, the condensed liquid is passed through a trap where the hydrocarbon rich layer will form. Drawing off the water rich layer will remove a portion of the water of formation while the remaining liquid (a mixture of alcohol and solvent) is returned to the reactor. In order to achieve the highest yield in the shortest possible time, use of a packed column having a large diameter to encourage high throughputs of liquid is preferred. If it is desired to recover unused vanadium components (for example, vanadium pentoxide) from the reaction vessel, this can be readily accomplished by filtering the contents of the reactor after the reaction is performed. If desired, the filtrate containing alcohol, solvent and possibly some product can be distilled to remove alcohol and solvent from the product to achieve the highest yield desired.

The present invention is illustrated by the Examples which follow.

EXAMPLES 1-7

The general procedure shown in each of the Examples used a one liter reactor equipped with a glass-lined Vigreaux distillation column having about a 2.5 cm. inner diameter and a height of 30 cm.

In each run the vanadium pentoxide reagent contained a differing content of vanadium (V) species under +5 valence. The following ingredients were used in each run, unless noted otherwise:

| Ingredient | Amount |
|---|---|
| Isobutanol | 333.0 gm. |
| Vanadium pentoxide | 91.0 gm. |

-continued

| Ingredient | Amount |
|---|---|
| Heptane solvent | 150.0 gm. |
| Urea catalyst | 4.5 gm. |
| Ammonium carbonate catalyst | 4.5 gm. |

The resulting mixture was heated to reflux so the heptane entrained the water of reaction as it formed. Vapor comprising isobutanol, heptane and water was condensed with water being further phase separated in a trap. The isobutanol and heptane were returned to the reaction vessel.

The reaction was generally continued until no further by-product water was formed which indicated substantial completion of the reaction.

The following Table gives the results obtained which demonstrate the adverse effect lower valence vanadium (e.g., $V^{+4}$) has on the yield of triisobutyl vanadate. The yields were calculated from the actual isolated product where possible or estimated from the quantity of water formed where the product was not isolated.

| Example | $V^{+4}$ (%) | % Yield of Vanadate |
|---|---|---|
| 1 | 0.87 | 53.5 |
| 2 | 0.71 | 48.0 |
| 3 | 0.38 | 67.0 |
| 4 | 0.24 | 78 |
| 5 | 0.19 | 85 |
| 6 | 0.10 | 92 |
| 7 | 0.08 | 98 |

Notes:
In Example 1 recovered solvent from an earlier run was employed. The weights of heptane and isobutanol was only approximated as 150 gm. and 333 gms., respectively.
Example 2 used 5.0 gm. of urea catalyst as well as vanadium pentoxide from a different supplier.
Example 3 used 5.0 gm. of ammonium carbonate.

What is claimed:

1. In a process for the manufacture of alkyl vanadates by the reaction of vanadium pentoxide with an alkyl alcohol in the presence of an azeotroping solvent to assist in the removal of by-product water, wherein the improvement comprises lowering in the vanadium pentoxide to be reacted, prior to the reaction, the amount of vanadium having a valence of lower than +5 in order to achieve an increased yield of alkyl vanadate formed by the reaction.

2. A process as claimed in claim 1 wherein the azeotroping solvent is an alkane solvent.

3. A process as claimed in claim 2 wherein the solvent is heptane.

4. A process as claimed in any of claims 1-3 wherein the reaction is carried out in the presence of an effective amount of a catalyst.

5. A process as claimed in any of claims 1-3 wherein the reaction is carried out in the presence of an effective amount of a basic nitrogenous catalyst.

6. A process as claimed in any of claims 1-3 wherein the reaction is carried out in the presence of an effective amount of a basic nitrogenous catalyst and the amount of vanadium having a valence lower than +5 is lowered to no more than about 0.2%, by weight of the vanadium pentoxide.

7. A process as claimed in any of claims 1-3 wherein the reaction is carried out in the presence of an effective amount of a basic nitrogenous catalyst, the amount of vanadium having a valence lower than +5 is lowered to no more than about 0.2%, by weight of the vanadium pentoxide, and the alkyl alcohol contains a $C_2$–$C_6$ alkyl group.

8. In a process for the manufacture of alkyl vanadates by the reaction of vanadium pentoxide with an alkyl alcohol in the presence of an azeotroping solvent to assist in the removal of by-product water, wherein the improvement comprises conducting the reaction using vanadium pentoxide containing a lowered amount of vanadium having a valence of lower than +5 in order to achieve an increased yield of alkyl vanadate formed by the reaction.

9. A process as claimed in claim 8 wherein the azeotroping solvent is an alkane solvent.

10. A process as claimed in claim 9 wherein the solvent is heptane.

11. A process as claimed in any of claims 8–10 wherein the reaction is carried out in the presence of an effective amount of a catalyst.

12. A process as claimed in any of claims 8–10 wherein the reaction is carried out in the presence of an effective amount of a basic nitrogenous catalyst.

13. A process as claimed in any of claims 8–10 wherein the reaction is carried out in the presence of an effective amount of a basic nitrogenous catalyst and the amount of vanadium having a valence lower than +5 is present at no more than 0.2%, by weight of the vanadium pentoxide.

14. A process as claimed in any of claims 8–10 wherein the reaction is carried out in the presence of an effective amount of a basic nitrogenous catalyst, the amount of vanadium having a valence lower than +5 is present at no more than about 0.2%, by weight of the vanadium pentoxide, and the alkyl alcohol contains a $C_2$–$C_6$ alkyl group.

* * * * *

UNITED STATES PATENT AND TRADEMARK OFFICE
CERTIFICATE OF CORRECTION

PATENT NO. : 4,465,636

DATED : August 14, 1984

INVENTOR(S) : Alan J. Abramson; Gershon J. Davis

It is certified that error appears in the above—identified patent and that said Letters Patent is hereby corrected as shown below:

Col. 6, line 11, -- about -- should appear before "0.2%".

Signed and Sealed this

Fifth Day of February 1985

[SEAL]

Attest:

DONALD J. QUIGG

Attesting Officer     Acting Commissioner of Patents and Trademarks